United States Patent
Wennerbäck

(10) Patent No.: US 8,109,916 B2
(45) Date of Patent: Feb. 7, 2012

(54) ABSORBENT ARTICLE COMPRISING AN ELASTIC LAMINATE

(75) Inventor: Margareta Wennerbäck, Mölnlycke (SE)

(73) Assignee: SCA Hygiene Products AB, Gothenberg (SE)

( * ) Notice: Subject to any disclaimer, the term of this patent is extended or adjusted under 35 U.S.C. 154(b) by 301 days.

(21) Appl. No.: 12/446,297

(22) PCT Filed: Nov. 13, 2006

(86) PCT No.: PCT/SE2006/050471
§ 371 (c)(1),
(2), (4) Date: Apr. 20, 2009

(87) PCT Pub. No.: WO2008/060205
PCT Pub. Date: May 22, 2008

(65) Prior Publication Data
US 2010/0324513 A1    Dec. 23, 2010

(51) Int. Cl.
*A61F 13/15* (2006.01)
(52) U.S. Cl. ......... 604/385.24; 604/385.25; 604/385.26; 604/385.3; 604/385.31; 604/396
(58) Field of Classification Search ............ 604/385.24, 604/385.25, 385.26, 385.3, 385.31, 396
See application file for complete search history.

(56) References Cited

U.S. PATENT DOCUMENTS

| | | |
|---|---|---|
| 3,424,162 A | 1/1969 | Parravicini |
| 4,119,450 A | 10/1978 | Bianco |
| 4,663,220 A * | 5/1987 | Wisneski et al. ............. 428/221 |
| 4,698,261 A | 10/1987 | Bothe et al. |
| 4,739,012 A | 4/1988 | Hagman |
| 4,777,080 A | 10/1988 | Harris, Jr. et al. |
| 4,842,596 A | 6/1989 | Kielpikowski et al. |
| 4,932,949 A | 6/1990 | Thygesen et al. |
| 5,114,781 A * | 5/1992 | Morman ....................... 428/198 |
| 5,143,679 A | 9/1992 | Weber et al. |
| 5,156,793 A | 10/1992 | Buell et al. |
| 5,167,897 A | 12/1992 | Weber et al. |
| 5,261,899 A | 11/1993 | Visscher et al. |

(Continued)

FOREIGN PATENT DOCUMENTS

CO    2007-003796 A    1/2008

(Continued)

OTHER PUBLICATIONS

Hildeberg et. al, Copending U.S. Appl. No. 11/630,371, filed Dec. 21, 2006 entitled "Absorbent Article Comprising an Elastic Laminate Material".

(Continued)

Primary Examiner — Jacqueline F. Stephens
(74) Attorney, Agent, or Firm — Buchanan Ingersoll & Rooney PC

(57) ABSTRACT

A pant-type absorbent article (55) includes a chassis structure, the chassis structure including a front panel (56), a back panel and a crotch panel (58) arranged between the front and back panels (56,57) and front and back waist panels (61a, 61b) arranged at the front and back panels (56,57) respectively. At least one of the front and back panels (56,57) includes an activated three-layer elastic laminate (68) including a first fibrous nonwoven web and a second fibrous nonwoven web and an elastic film between the first and second fibrous nonwoven webs. At least one of the first and second fibrous nonwoven webs is a creped nonwoven web.

15 Claims, 3 Drawing Sheets

U.S. PATENT DOCUMENTS

| | | |
|---|---|---|
| 5,336,545 A | 8/1994 | Morman |
| 5,422,172 A | 6/1995 | Wu |
| 5,440,764 A | 8/1995 | Matsushita |
| 5,462,541 A | 10/1995 | Bruemmer et al. |
| 5,514,470 A * | 5/1996 | Haffner et al. ............... 428/343 |
| 5,592,690 A | 1/1997 | Wu |
| 5,628,738 A | 5/1997 | Suekane |
| 5,634,216 A | 6/1997 | Wu |
| 5,635,290 A | 6/1997 | Stopper et al. |
| 5,706,524 A | 1/1998 | Herrin et al. |
| 5,733,628 A | 3/1998 | Pelkie |
| 5,746,730 A | 5/1998 | Suzuki et al. |
| 5,769,838 A | 6/1998 | Buell et al. |
| 5,861,074 A | 1/1999 | Wu |
| 5,921,973 A | 7/1999 | Newkirk et al. |
| 6,072,005 A | 6/2000 | Kobylivker et al. |
| 6,106,925 A | 8/2000 | Palumbo |
| 6,210,386 B1 | 4/2001 | Inoue |
| 6,240,569 B1 | 6/2001 | van Gompel et al. |
| 6,476,289 B1 | 11/2002 | Buell et al. |
| 6,540,731 B2 | 4/2003 | Magnussson et al. |
| 6,552,245 B1 | 4/2003 | Roessler et al. |
| 6,585,713 B1 * | 7/2003 | LeMahieu et al. ............ 604/392 |
| 6,627,564 B1 | 9/2003 | Morman et al. |
| 6,914,018 B1 | 7/2005 | Uitenbroek et al. |
| 7,722,591 B2 | 5/2010 | Back |
| 2002/0002021 A1 | 1/2002 | May et al. |
| 2002/0019187 A1 | 2/2002 | Carroll et al. |
| 2002/0029026 A1 | 3/2002 | Furuya et al. |
| 2002/0052591 A1 | 5/2002 | Zehner et al. |
| 2003/0022582 A1 | 1/2003 | Cree et al. |
| 2003/0078558 A1 | 4/2003 | Karami et al. |
| 2004/0078018 A1 | 4/2004 | Van Gompel et al. |
| 2004/0102746 A1 | 5/2004 | Mortell et al. |
| 2004/0116887 A1 | 6/2004 | Thorson et al. |
| 2004/0122405 A1 | 6/2004 | Van Gompel et al. |
| 2004/0122406 A1 | 6/2004 | Moser et al. |
| 2004/0127878 A1 | 7/2004 | Olson et al. |
| 2004/0133180 A1 | 7/2004 | Mori et al. |
| 2004/0192140 A1 | 9/2004 | Schneider et al. |
| 2004/0197588 A1 | 10/2004 | Thomas et al. |
| 2004/0241389 A1 | 12/2004 | Chung et al. |
| 2004/0243086 A1 | 12/2004 | Van Gompel et al. |
| 2005/0010186 A1 | 1/2005 | Otsubo et al. |
| 2005/0101216 A1 | 5/2005 | Middlesworth et al. |
| 2005/0106980 A1 | 5/2005 | Abed et al. |
| 2006/0148358 A1 | 7/2006 | Hall et al. |
| 2007/0233034 A1 | 10/2007 | Hildeberg et al. |
| 2008/0000003 A1 | 1/2008 | Melander |
| 2008/0033387 A1 | 2/2008 | Wastlund-Karlson et al. |
| 2009/0306616 A1 | 12/2009 | Wennerback |
| 2010/0036355 A1 | 2/2010 | Hakansson et al. |

FOREIGN PATENT DOCUMENTS

| | | |
|---|---|---|
| EP | 0 287 388 A2 | 10/1988 |
| EP | 0 304 957 A2 | 3/1989 |
| EP | 0 360 929 A1 | 4/1990 |
| EP | 0 409 307 B1 | 1/1991 |
| EP | 0 418 493 A1 | 3/1991 |
| EP | 0 486 006 B1 | 9/1996 |
| EP | 0 861 647 A2 | 9/1998 |
| EP | 0714351 B1 | 12/1998 |
| EP | 0 605 012 B1 | 3/1999 |
| EP | 0 604 731 B1 | 6/1999 |
| EP | 1 184 022 | 3/2002 |
| EP | 1 035 818 B1 | 4/2002 |
| EP | 1 384 459 A2 | 7/2003 |
| EP | 1 473 008 | 11/2004 |
| FR | 2 586 558 | 3/1987 |
| FR | 2 810 879 | 1/2002 |
| GB | 2 284 538 A | 6/1995 |
| JP | 06255006 A | 9/1994 |
| JP | 07-252762 | 10/1995 |
| JP | 9-286085 | 11/1997 |
| JP | 10-043235 A | 2/1998 |
| JP | 2002 058 703 A | 2/2002 |
| JP | 2002-065740 | 3/2002 |
| JP | 2002-172137 A | 6/2002 |
| JP | 2002-520090 T | 7/2002 |
| JP | 2002-273808 A | 9/2002 |
| JP | 2003-520146 | 7/2003 |
| JP | 2003-290284 | 10/2003 |
| JP | 2004-50621 A | 2/2004 |
| JP | 2004-98356 A | 4/2004 |
| JP | 2004-519270 | 7/2004 |
| RU | 965339 | 10/1982 |
| RU | 2 008 774 | 3/1994 |
| RU | 2 221 531 | 1/2004 |
| TW | 233473 | 11/1994 |
| WO | WO 95/19258 | 7/1995 |
| WO | WO 96/10979 A1 | 4/1996 |
| WO | WO 97/29722 A1 | 8/1997 |
| WO | WO 97/34037 A1 | 9/1997 |
| WO | WO 98/37847 A1 | 9/1998 |
| WO | WO 99/27876 A1 | 6/1999 |
| WO | WO 99/32164 A1 | 7/1999 |
| WO | WO 00/02511 A1 | 1/2000 |
| WO | WO 00/45764 A1 | 8/2000 |
| WO | WO 01/30563 A1 | 5/2001 |
| WO | WO 01/45927 A1 | 6/2001 |
| WO | WO 01/53076 | 7/2001 |
| WO | WO 02/34185 | 5/2002 |
| WO | WO 02/49560 A1 | 6/2002 |
| WO | WO 03/004748 A1 | 1/2003 |
| WO | WO 03/019714 A1 | 3/2003 |
| WO | WO 03/047488 A1 | 6/2003 |
| WO | WO 2004/058120 | 7/2004 |
| WO | WO 2004/060251 A1 | 7/2004 |
| WO | WO 2004/078083 A1 | 9/2004 |
| WO | WO 2005/095700 A1 | 10/2005 |
| WO | WO 2005/122984 A1 | 12/2005 |
| WO | WO 2005/122985 A1 | 12/2005 |
| WO | WO 2006/038837 A1 | 4/2006 |
| WO | WO 2006/093439 A1 | 9/2006 |
| WO | WO 2006/093440 A1 | 9/2006 |
| WO | WO 2006/093443 A1 | 9/2006 |
| WO | WO 2007/114744 A1 | 10/2007 |
| WO | WO 2008/060194 A1 | 5/2008 |

OTHER PUBLICATIONS

Karlson et al., Copending U.S. Appl. No. 11/576,497, filed Dec. 3, 2008 entitled "Absorbent Article Comprising an Elastic Web Material".

Wastlund-Karlssson et al., Copending U.S. Appl. No. 11/630,372, filed Dec. 21, 2006 entitled "Absorbent Article Comprising an Elastic Laminate".

Melander, Copending U.S. Appl. No. 11/845,153, filed Aug. 27, 2007 entitled "Underwear Article Comprising an Elastic Laminate".

Norrby et al., Copending U.S. Appl. No. 12/447,694, filed Apr. 29, 2009 entitled "Elastic Laminate and Absorbent Article Comprising the Laminate".

Wennerback, Copending U.S. Appl. No. 12/514,086, filed May 8, 2009 entitled "Absorbent Article Comprising an Elastic Laminate Material".

Non-Final Office Action in Copending U.S. Appl. No. 11/630,372 to Wastlund-Karlson et al. dated Sep. 16, 2009.

Final Office Action in Copending U.S. Appl. No. 11/630,372 to Wastlund-Karlson et al. dated Mar. 2, 2008.

Non-Final Office Action in Copending U.S. Appl. No. 11/630,372 to Wastlund-Karlson et al. dated Jul. 8, 2009.

Non-Final Office Action in Copending U.S. Appl. No. 11/630,371 to Hildeberg et al. dated Oct. 5, 2009.

Sueo Kawabata, "The Standardization and Analysis of Hand Evaluation", Second Edition, The Hand Evaluation and Standardization Committee, The Textile Machinery Society of Japan, published by the Textile Machinery Society of Japan, Osaka, Japan, Jul. 1980—Textile Machinery Japan.

An English Translation of the Notice of Reasons for Rejection issued in the corresponding Japanese Patent Application No. 2007-517994 dated Nov. 24, 2009.

International Search Resort (PCT/ISA/210), Jun. 21, 2007.

Written Opinion (PCT/ISA/237) Jun. 29, 2007.

* cited by examiner

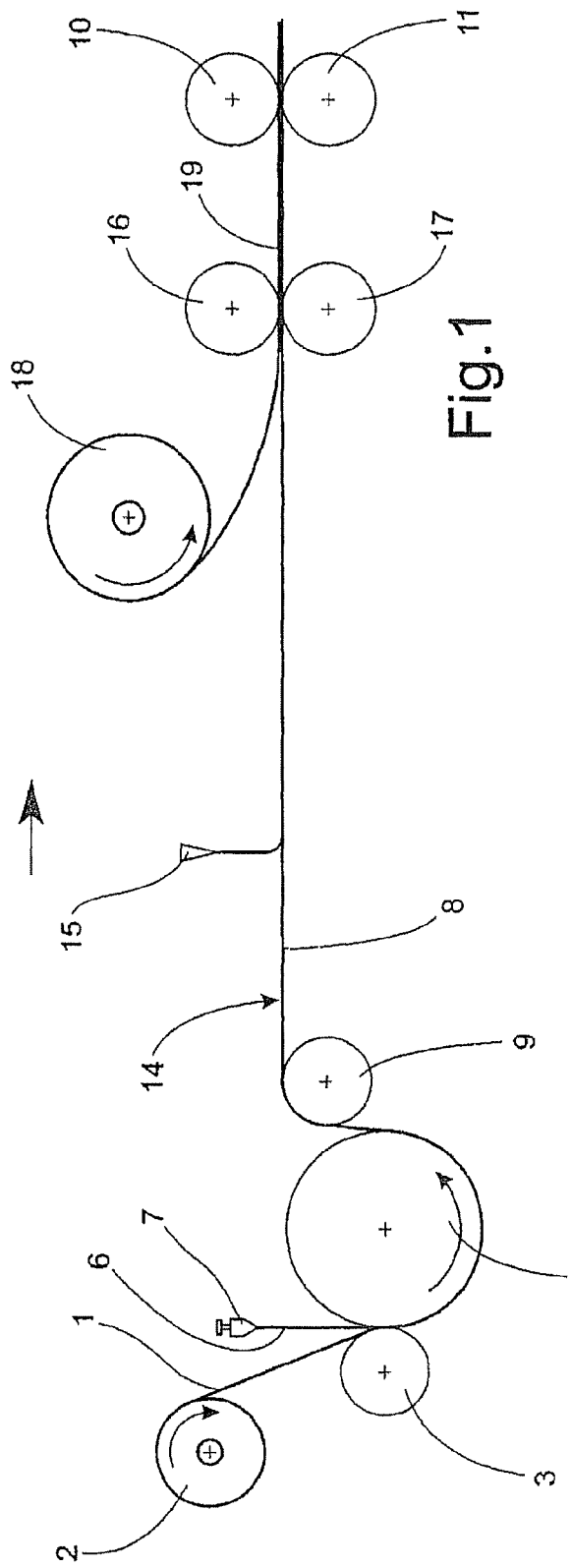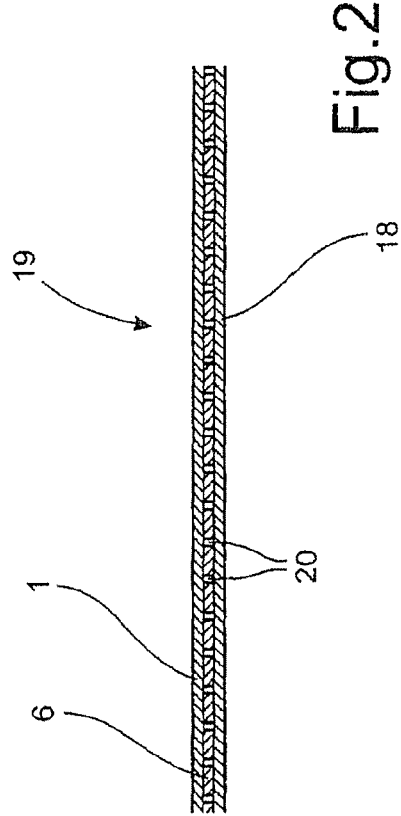

ABSORBENT ARTICLE COMPRISING AN ELASTIC LAMINATE

TECHNICAL FIELD

The invention relates to a pant-type absorbent article comprising an at least partially elastic chassis structure, the chassis structure comprising a front panel, a back panel and a crotch panel arranged between the front and back panels. At least one of the front and back panels comprises an activated three-layer elastic laminate comprises a first fibrous nonwoven web and a second fibrous nonwoven web and an elastic film between the first and second fibrous nonwoven webs.

BACKGROUND ART

Pant-type absorbent articles include a pant-shaped chassis structure and an absorbent core component integrated with the chassis. A major objective when designing pant articles is to make them resemble ordinary underwear as closely as possible. Hence, absorbent articles such as pant diapers, sanitary pants and incontinence pants are designed to fit comfortably and snugly about the wearer. It is desirable that the articles are capable of being pulled up and down over the hips of the wearer to allow the wearer or caregiver to easily remove a soiled article and to replace it with a new clean one. For these reasons, the article chassis is usually made of a material that is elastically stretchable, at least in the areas intended to be applied over the wearer's hips. Furthermore, it is desirable that the chassis surrounding the absorbent parts of the pant-type article is permeable to air and vapour, i.e. that it is breathable. A breathable article prevents moisture from remaining on the skin of the wearer and is more comfortable and less warm to wear than a non-breathable article. It is also beneficial if the article is soft, smooth and textile-like, so that it does not chafe the skin of the wearer and so that it resembles ordinary underwear as closely as possible.

Moreover, it is important that the absorbent pant article can be pulled up over the hips of a wearer without rupturing. A common problem is that the wearer or the caregiver tears the pant by inadvertently poking the fingers through the material when trying to get a good grip for pulling up or removing the pant.

A previously used elastic material for pant articles is a laminate comprising an elastic film sandwiched between two layers of non-elastic nonwoven. In order to render the laminate elastically stretchable, it is subjected to an activation treatment. A three-layer, activated laminate is disclosed in International Patent Application No. WO 03/047488. The activated laminate is produced by incrementally stretching an elastic film layer between two non-elastic cloth-like layers. Incremental stretching is carried out by passing the laminate between intermeshing gear rollers. Activation of elastic laminates by incremental stretching is also disclosed in U.S. Pat. Nos. 5,143,679, 5,156,793 5,167,897, 5,422,172, 5,592,690, 5,634,216 and 5,861,074. The non-elastic cloth-like layers are fully or partially broken or torn during the activation process so that the elasticity of the laminate after activation is mainly governed by the elasticity of the elastic film layer. In the three-layer laminate in WO 03/047488, the non-elastic layers are completely broken so that the elasticity of the activated laminate is substantially the same as the elasticity of the elastic film layer.

The disclosed laminates have good comfort properties and are soft, textile-like, breathable and elastic. However, a major disadvantage with the known laminates is that the activation process at least partially breaks and destroys the cloth-like layers resulting in a material having decreased tensile strength and puncture resistance. When used as a chassis component in a disposable pant article, the material is easily torn when exposed to the forces arising when putting on or pulling off the pant article. This tearing problem is particularly pronounced for female wearers or caregivers who often have long fingernails that may penetrate and destroy the pant material.

In order to overcome the problem with low resistance to the stresses arising during use of an absorbent article including an elastic laminate, it has been suggested in US 2005/0101216 A1 to form an elastic laminate from an elastic film and a creped nonwoven. By using a creped nonwoven, the laminate will have the soft and lofty properties of the creped, bulky nonwoven. Moreover, the creped nonwoven is also said to render the laminate elastic as the nonwoven is extensible in the direction of creping. The use of a creped nonwoven is offered as an alternative to activation by incremental stretching. Hence, US 2005/0101216 A1 teaches that by using a creped nonwoven, the harsh activation treatment with its concomitant detrimental effect on the strength of the nonwoven web can be avoided.

However, although the creped nonwoven used in US 2005/0101216 A1 provides the laminates with some degree of elasticity, the elastic properties of the laminates are still severely limited by the extensibility of the creped nonwoven.

Hence, there still exists a need for an elastic laminate combining high tensile strength, softness, flexibility and puncture resistance. There is also a need for a pant-type absorbent article having a chassis with elastic panel portions having high tensile strength, softness, flexibility and puncture resistance.

Accordingly, an object of the invention is to provide an improved elastically stretchable laminate for use in disposable pant-type absorbent articles. Another object of the invention is to provide a textile-like disposable pant-type absorbent article having improved tensile strength and puncture resistance in combination with softness and flexibility. A further object of the invention is to offer a simple and economical method for the production of an elastically stretchable laminate having high tensile strength and textile-like appearance.

DISCLOSURE OF THE INVENTION

In accordance with the invention, there is provided a pant-type absorbent article comprising a chassis structure, the chassis structure comprising a front panel having a front end edge and first and second side edges, a back panel having a back end edge and first and second side edges and a crotch panel arranged between the front and back panels and front and back waist panels arranged at the front and back panels respectively, and an absorbent core being integrated with the chassis structure, the first and second side edges of the front panel being joined by edge joins to the corresponding first and second side edges of the back panel, wherein at least one of the front and back panels comprises an activated three-layer elastic laminate comprising a first fibrous nonwoven web and a second fibrous nonwoven web and an elastic film between the first and second fibrous nonwoven webs. At least one of the first and second fibrous nonwoven webs is a creped nonwoven web and the three-layer elastic laminate has a tensile strength in a first direction (MD) of at least 20 N/25 mm and preferably a tensile strength in the first direction (MD) of at least 25 N/25 mm and a tensile strength in a second direction (CD) perpendicular to the first direction (MD) of at least 15 N/25 mm and preferably a tensile strength in the second direction (CD) of at least 20 N/25 mm.

The first direction is normally the manufacturing direction, MD of the activated elastic laminate web and the second direction is normally the cross direction, CD. The three-layer elastic laminate is preferably incorporated in the pant-type absorbent article with the MD parallel to the waist edge of the article so that the waist opening can be elastically extended.

It is preferred that at least one of the waist panels of the pant-type article according to the invention comprises an elastic waist feature.

The waist panels can be joined to the front and back panels as separate components in a pant-forming process. The waist panels may comprise an elastic waist feature in the form of an elastic band of any suitable kind, such as elastic laminates, elastic foam strips, elastic nonwovens, non-elastic materials that have been elasticised with elastic threads or strings, etc. A commonly used elastic waist feature is made by attaching elastic elements such as threads, bands or strings in a pre-tensioned state between two layers of nonwoven, non-elastic material. All commonly used elastic materials such as natural or synthetic rubber, elastic foam, etc. can be employed. A waist feature of this type may be formed from two separate layers of nonwoven or may be made from a single layer of nonwoven that has been folded into a two-layer structure. It is also possible to use the activated laminate in accordance with the invention to create an elastic waist feature. The elastic waist feature in the waist panels preferably has a higher elastic tension than the elastic panel portions in other parts of the chassis. When forming the elastic waist feature from the activated laminate in accordance with the invention, it is preferred to use at least two plies of the laminate, for instance, by double-folding the laminate.

In an alternative embodiment, the elastic waist feature is an integral part of the chassis. In this embodiment, the elastic waist feature may have been formed by folding an edge portion of a non-elastic chassis web and attaching elastic elements between the folded portions of the chassis web. It is also possible to attach elastic elements to a layer of the chassis web and leave the elastic elements non-covered, or covered by a separate web. A further option is to create an elastic waist feature by folding an edge portion of an elastic front and/or back panel, thus creating a waist panel having higher elastic tension than the non-folded portions of the elastic panels. Elastic waist features suitable for use in the pant-type absorbent article in accordance with the invention are disclosed in PCT/SE205/000309.

The elastic waist panel preferably extends continuously all the way between the edge joins. In a particularly preferred embodiment, both the front and the back waist panels are elastic waist panels forming a continuous elastic waist band.

The elastic laminate used in accordance with the invention preferably forms the front and the back panels of the pant-type absorbent article. However, it is possible to make only parts of the respective front and back panel of the elastic laminate. In such embodiments, at least 20%, preferably at least 25%, more preferably at least 30% and most preferably at least 40% of the total surface area of the chassis as measured when the chassis is in a flat state is constituted by the elastic laminate. As an example, the elastic laminate may be used only in those parts of the front and back panels that are intended to lie over the wearer's hips and thus form elastic side panels. It may also be desirable to avoid overlap between the elastic laminate material and the portions of the chassis structure occupied by the absorbent core.

The absorbent core is preferably part of a separately produced core component or "core pack" that has been incorporated into the chassis structure. The core component comprises the absorbent core enclosed between a topsheet and a liquid impermeable backsheet. The core component can of course contain further components such as a liquid transport sheet, elastic members, shape-stabilizing members, shaping elements and the like.

Although forming the core component separately is a preferred way of incorporating an absorbent core in the chassis structure, alternative embodiments utilising parts of the chassis structure as topsheet and/or backsheet are also contemplated within the scope of the invention.

The elastically stretchable laminate may be produced by a method comprising laminating an elastic film between a first nonwoven web and a second nonwoven web, wherein at least one of the first and the second nonwoven webs is a creped nonwoven web and the laminate is rendered elastic by incremental stretching of the laminate in at least one direction. In accordance with the invention, the activation of the laminate by incremental stretching takes place after lamination, i.e. after the layers in the laminate have been bonded to each other.

In the laminate used in the pant-type absorbent article in accordance with the invention, at least one of the nonwoven webs is a creped nonwoven. Creped nonwovens generally have greater extensibility and flexibility than non-creped nonwovens. By choosing a creped nonwoven for one or both of the nonwoven layers, it is possible to achieve an elastic laminate that is more conformable, flexible and extensible than when using non-creped nonwovens. The creped nonwoven material makes it easier for the elastic laminate to contract after elongation, thus increasing the elasticity when compared to a corresponding laminate having only non-creped nonwoven layers.

By a creped nonwoven material is meant any nonwoven material wherein the fibres have been crinkled or bulked, thermally or mechanically, to foreshorten the fibres in the direction of creping whereby the material becomes stretchable and preferably resiliently stretchable in the direction of the creped fibres. The nonwoven webs used in the invention may be creped both in the manufacturing direction, MD and in the cross direction CD. The creped nonwoven webs are preferably stretchable, more preferably resiliently or elastically stretchable in at least the MD implying that the webs will recover at least some of their initial dimensions after being stretched. If it is desirable to have stretch properties both in MD and CD, this may be achieved either by choosing a nonwoven web that is inherently CD stretchable or by two-directional creping. Recovery from stretching is strongly dependent of the fibre orientation. Hence, a web that is stretchable in the MD and has a majority of the fibres oriented in that direction will have better recovery properties than a more randomised web.

By using webs that have been made stretchable by creping, it is possible to choose any conventional nonwoven web having high tensile strength in the CD. This is a great advantage since nonwoven webs that are stretchable due to their fibrous composition usually have low tensile strength in the CD. Such webs are also relatively expensive, which make them less suitable for use in disposable articles.

Further, it has now been found that by using at least one creped nonwoven web in the laminate, the laminate can be activated by incremental stretching and still retain its tensile strength to a much higher degree than when using non-creped nonwoven materials. The stretchable, creped nonwoven webs are not destroyed by the activation process, but remain largely unbroken.

The activation step involves incremental stretching of the two-layer laminate. Activation can be carried out by means of heated or non-heated intermeshing gear rollers having circumferentially arranged teeth that intermesh and thereby stretch the laminate. The activation step allows the laminate to be subsequently stretched without being appreciably restrained by the nonwoven web.

The layers in the laminate can be bonded to each other by any suitable bonding method, such as adhesively, thermally or ultrasonically. However, in accordance with one particularly suitable embodiment of the invention, the elastic film is extrusion coated onto at least one of the first and second fibrous nonwoven webs.

The elastic film is preferably perforated in order to provide breathability. This can be achieved directly in conjunction with the lamination process if at least one of the nonwoven webs is bonded to the elastic film by means of extrusion coating. The perforating step can be carried out by passing the combined elastic film and nonwoven web over a vacuum lamination drum while the elastic film is in a molten or semi-molten state. Such a process is disclosed in U.S. Pat. No. 5,733,628 and results in the elastic film being formed into a three-dimensional apertured laminate layer.

Alternatively, the elastic film can be a prefabricated perforated film that is bonded to the nonwoven webs by any suitable means such as adhesively, thermally or with ultrasonic welding.

The elastic film may have a basis weight of between 10 and 120 g/m$^2$, preferably between 15 and 60 g/m$^2$ and may be of any suitable elastic polymer, natural or synthetic. Some examples of useful materials for the elastic layer are low crystallinity polyethylenes, metallocene-catalyzed low crystallinity polyethylenes, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. One example of a suitable elastic film is an apertured three-layer elastomeric film with the composition polyethylene-styrene/ethylene/butadiene/styrene-polyethylene (PE-SEBS-PE).

In this context, an elastic material is defined as a material having a permanent elongation after relaxation of less than 10% after the material has been subjected to an elongation of 30% in the elasticity test specified in the description.

A non-elastic material is a material that does not fall within the definition of an elastic material. Accordingly, a non-elastic material as used herein is a material that may be stretchable or non-stretchable. In the case of a stretchable material, the material has a permanent elongation after stretching and relaxation of more than 10% after having been subjected to an elongation of 30% as determined according to the elasticity test.

The laminate used in the pant-type absorbent article according to the invention is preferably continuously produced from webs running in a machine direction, MD, and the laminate is preferably activated by incremental stretching in at least the MD. By subjecting the laminate to activation only in the MD, the creped nonwoven material in the activated laminate will retain maximum tensile strength in the cross direction, CD, perpendicular to the MD and to the direction of elastic extensibility of the activated laminate. However, it is usually desired to have some degree of stretch also in the CD. As has been mentioned above, CD stretchability can be obtained by choosing an inherently stretchable material or by creping and/or the web also in the CD. The creped nonwoven material acts as a reinforcement of the laminate in the CD, rendering the laminate resistant to tearing and particularly suitable for use as an elastic panel material in a pant-type absorbent article.

The laminate webs can be of equal width to produce a three-layer laminate that can be subsequently continuously introduced in the manufacturing process for a disposable pant-type article and form elastic portions of the article chassis. Alternatively, the laminate can be cut and shaped into separate elements that can be subsequently used to produce a disposable pant-type absorbent article.

In accordance with one embodiment of the invention, one of the first and the second nonwoven webs has a width equal to the width of the elastic film and the other of the first and the second nonwoven webs has a width greater than the width of the elastic film. Such a three-layer laminate is suitably continuously introduced in the process when producing disposable pant-type articles and may form both elastic and non-elastic portions of the article chassis. For instance, the nonwoven web portion extending outside of the laminate web may be used to create a waist panel on the pant-type article. The waist panel preferably is an elastic waist panel, implying that the non-elastic nonwoven web has to be provided with elastic elements such as bands, strings, etc.

One or both of the fibrous nonwoven webs in the elastic laminate may preferably comprise thermoplastic fibres. Examples of suitable polymers for use in the nonwoven webs are polyethylene, polyesters, polypropylene and other polyolefin homopolymers and copolymers. Particularly well suited nonwoven webs are those comprising thermoplastic fibres that are a mixture of polypropylene and polyethylene fibres. The preferred webs have a high content of thermoplastic fibres and contain at least 50% thermoplastic fibres and preferably at least 80% thermoplastic fibres. The nonwoven webs will typically be incorporated in joins and seams in a disposable pant-type article. Hence, it is highly desirable that the nonwoven webs be weldable by heat or by ultrasonic welding processes.

The fibrous layers are preferably chosen so as to provide a soft and cloth-like feel and appearance to the laminate. Examples of suitable materials are meltblown or spunbond nonwovens. However, any soft, flexible and preferably extensible nonwoven materials and nonwoven laminates may be used, such as Spunbond-Meltblown-Spunbond-laminates (SMS), carded bonded webs and spunlaced materials.

The basis weight of the creped nonwoven webs used in the laminate is suitably from 10-80 g/m$^2$ and preferably from 13-50 g/m$^2$. Examples of suitable polymers used in the fibrous material are polyethylene, polyesters, polypropylene and other polyolefin homopolymers and copolymers. Natural fibres, for example cotton, may also be used as long as they provide the desired properties. A mixture of polymers can contribute to a higher flexibility of the nonwoven layer, and through this, give the nonwoven material a higher elongation at maximum load. A mixture of polyethylene and polypropylene polymers has proven to provide good results in this respect. A mixture of fibres of different polymers is also possible.

BRIEF DESCRIPTION OF DRAWINGS

The invention will in the following be described in greater detail with reference to the appended drawings, wherein FIG. 1 shows a laminating process in accordance with the invention, FIG. 2 shows a three-layer laminate in accordance with the invention.

EMBODIMENTS OF THE INVENTION

Figure 3:
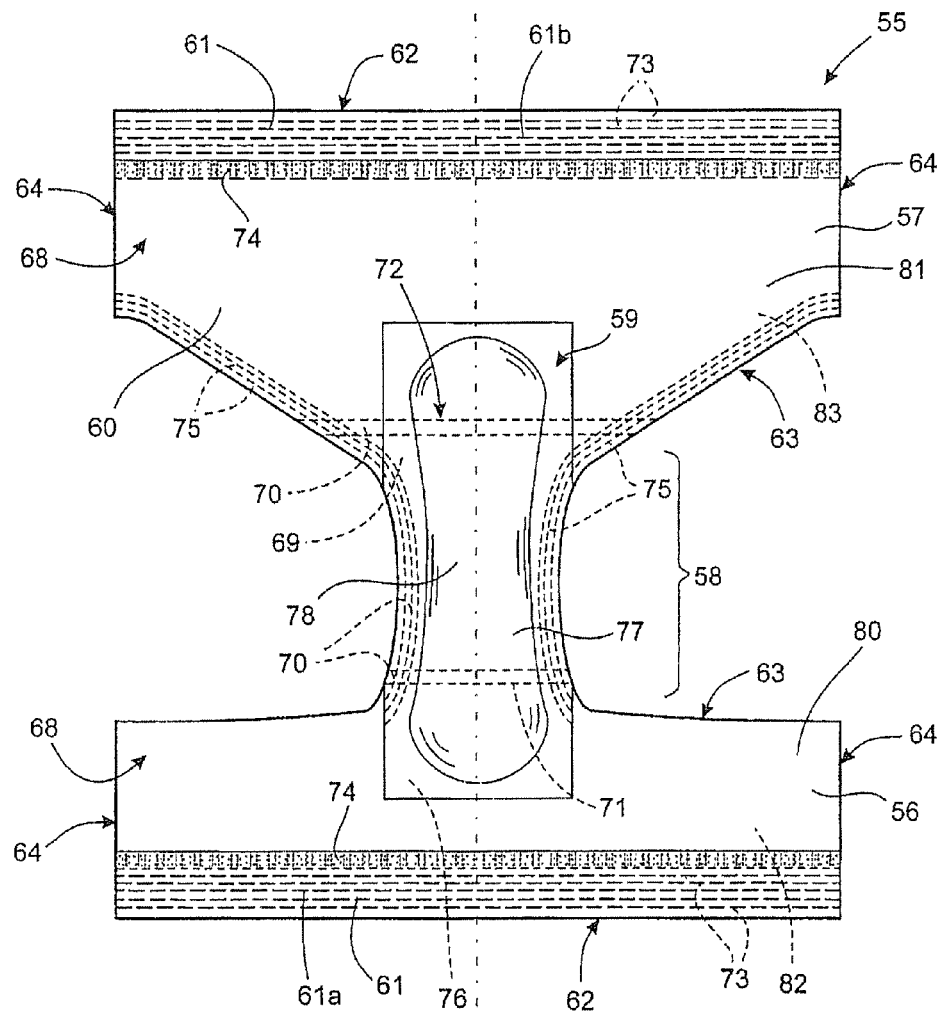
FIG. 3 shows a planar view of a pant diaper with the side joins open.

FIG. 1 shows schematically a method for producing an elastically stretchable three-layer laminate in accordance with the invention. A first nonwoven web 1 is fed from a storage roll 2 into a first bonding nip between a rubber roll 3 and a metal roll 4. A molten elastic film-forming polymer 6 is extruded through a die 7 into the nip and the first non-elastic nonwoven web 1 and the elastic film forms a first laminate 8 that is taken off at roller 9.

In a second lamination step, the film-side 14 of the first laminate 8 is coated or sprayed with adhesive and is subsequently passed through a second bonding nip between two bonding rollers 16,17 together with a second nonwoven web 18. The adhesive is preferably a thermoplastic adhesive, although other types of adhesives may be used if so desired. In accordance with the invention, one of the first and second nonwoven webs 1,18 is a creped nonwoven.

The three-layer laminate 19 is subsequently activated by passing the laminate between intermeshing gear rollers 10,11 so that the three-layer laminate 19 is subjected to incremental stretching. A number of different stretching techniques exist, as set out in EP 0 714 351. Depending on the design of the intermeshing gear rollers, the incremental stretching can be made to stretch the laminate diagonally, in the machine direction, MD, or in the cross direction, CD. The amount of breakage of the nonwoven webs caused by the incremental stretching can be controlled by adjusting the intermeshing depth of the teeth or intermeshing elements on the gear rollers. The incremental stretching releases or activates the elasticity of the elastic film and allows the three-layer laminate 19 to be elastically extensible.

The metal roll 4 in the first bonding nip is preferably an apertured suction roll so that three-dimensional forming and aperturing of the extruded elastic film 6 is achieved simultaneously with bonding of the film 6 to the first nonwoven web 1.

The second lamination step can, alternatively be carried out by thermal or ultrasonic bonding.

FIG. 1 is a highly schematic representation of the method according to the invention. However, all individual method steps are well known and have previously been described in the art. Further, FIG. 1 does not show the widths of the individual webs. The laminate material can be made with all webs having the same width or CD extension. Alternatively, the second nonwoven web 18 can have a greater width than the elastic film 6 and the first nonwoven web 1 and may extend past the first laminate on one or both sides thereof.

The three-layer laminate 19 shown in FIG. 2 comprises a first fibrous nonwoven layer 1, a second nonwoven layer 18 and an elastic film 6 between the first and second nonwoven layers 1,18. The elastic film 6 is apertured and has a multiplicity of apertures 20 arranged therethrough. The apertures 20 may be three-dimensionally formed apertures as disclosed in WO 03/047488 or may be simple two-dimensional holes through the film 6.

The elastic film 6 is elastically extensible at least in a first direction, MD. For a laminate produced in a continuous process, the first direction, MD is the machine direction, i.e. the travelling direction of the laminate web during production of the web. The laminate 19 is preferably elastically extensible in the first direction MD and preferably extensible or elastically extensible in a second direction, the cross direction, CD, perpendicular to the first direction MD.

The layers of the laminate 19 may be bonded to each other by any suitable means such as extrusion bonding, adhesively, or by thermal bonding with application of heat or ultrasound.

In accordance with the invention, at least one of the first and second nonwoven layers 1,18 is a creped nonwoven material.

The activated three-layer laminate 19 is soft and drapable, with high tensile strength and puncture resistance and is exceptionally well suited for use in different kinds of disposable pant-type articles. The creped nonwoven material provides reinforcement of the laminate, particularly perpendicularly to the direction of stretch. Hence, the laminate is puncture resistant and can be subjected to the pulling and stretching forces arising when putting on and taking off a pant article without breaking or tearing.

Moreover, by selecting nonwoven materials having thermoplastic properties, it is possible to obtain a laminate that can be readily incorporated in a disposable article by thermo-welding techniques. Since thermo-bonds used in side joins usually penetrate the welded materials, the orientation of the laminate with respect to the first and second nonwoven layers is normally not crucial for obtaining a thermobonded join as long as at least one of the layers is predominantly made of thermoplastic fibres or the combination of the two layers contain sufficient thermoplastic material in order to achieve satisfactory bond strength.

Figure 4:
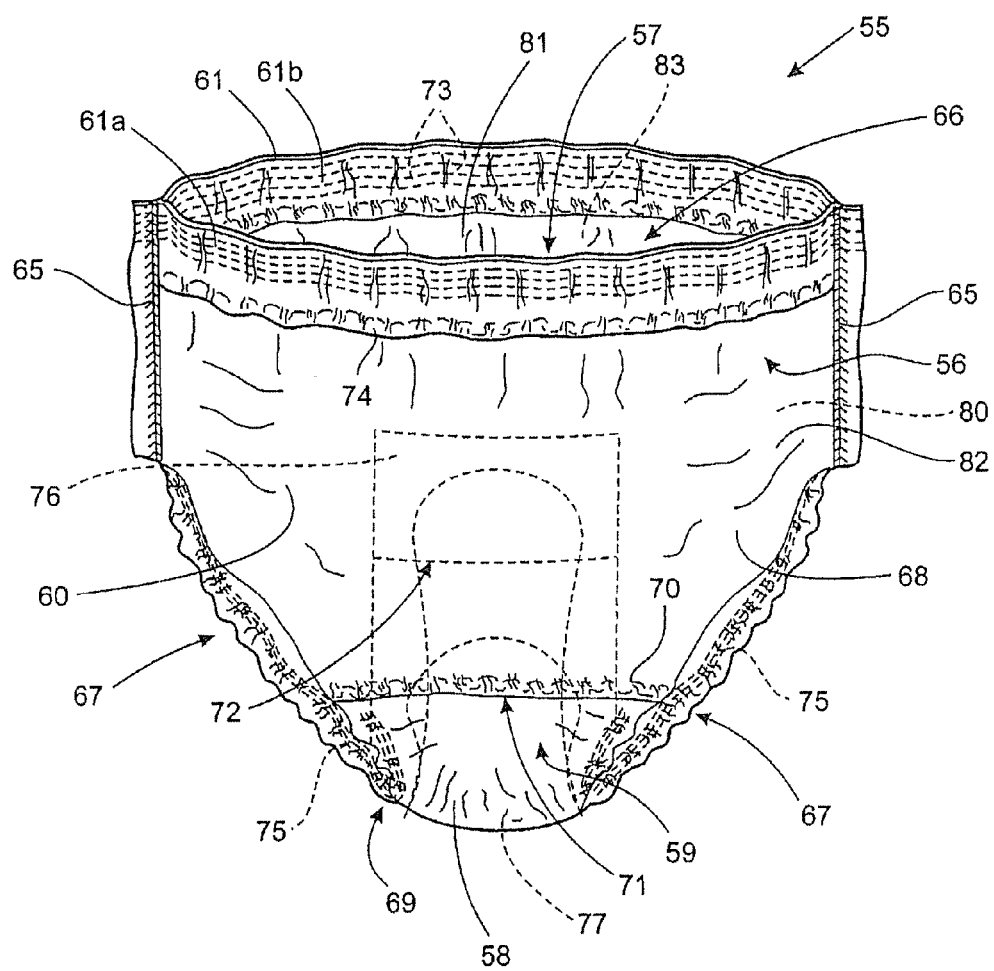
FIG. 4 shows the diaper in FIG. 3 with closed side joins.

The pant diaper 55 shown in FIGS. 3 and 4 is designed to enclose the lower part of a wearer's trunk like conventional underwear. In FIG. 3, the diaper 55 is shown from the inside, i.e. from the side facing the wearer when the article is being worn and in FIG. 4, the diaper is shown from the outside, or the garment-facing side, which is the side that is facing away from the wearer when the diaper is being worn.

The diaper has a front panel 56, a back panel 57 and a crotch panel 58 extending between the front and back panels 56,57 and having a relatively narrow width as compared to the front and back panels 56,57. The front and back panels 56,57 are arranged to cover the wearer's hips and to extend over the belly and the back of the wearer to encircle the lower part of the wearer's trunk.

The diaper 55 further comprises a core region 59 extending from the crotch panel 58 into the front panel 56 and the back panel 57. The front and back panels 56,57 form part of a chassis 60 that extends on the garment-facing side of the diaper 55 and covers and surrounds the core region 59. The chassis 60 comprises the front panel 56, the back panel 57, the crotch panel 58 and an elastic waist band 61 secured to the front and back panels 56,57. Each of the front and back panels 56,57 has a waist edge 62 a crotch edge 63 and a pair of side edges 64 respectively.

The term "panel" is used herein to denote a functional part of the diaper chassis while the terms "region" and "portion" are used to denote the location of a particular feature of the diaper in the chassis or to describe the intended positioning of a particular part of the diaper in relation to a user's body. A panel may be a separate component or an integrated part of the chassis. A region or portion may have an extension fully or partially covering one or more panels.

When components are joined, attached or secured to each other they are separate parts that have been bonded by any suitable means such as adhesively, by stitching or by ultrasonic welding or thermo-welding. The term joined also includes separable (openable) joins, such as separable side joins and reclosable joins such as hook-and-loop joins, reclosable tape joins, snap fasteners, etc. Components that have been arranged on each other need not be bonded, although as used herein, the term "arranged" should be understood broadly to also include bonded components.

The front and back panels 56,57 are joined to each other along their side edges 64 by thermobonding, ultrasonic welding, glue strings or the like to form side seams 65, as shown in FIG. 4. The elastic waist band 61 consists of a front waist panel 61*a* and a back waist panel 61*b*, which are secured to the front panel 56 and the back panel 57, respectively. The front and back waist panels 61*a*, 61*b* are also joined to each other along the side seams 65. By joining the front and back panels 56, 57 and the waist panels 61*a*, 61*b*, the pant diaper 55 is provided with a waist opening 66 and a pair of leg openings 67.

FIG. 3 shows the diaper 55 in a flat state with all elastic components that have been attached to the chassis 60 under tensional stress drawn out to the full non-tensioned dimensions of the chassis 60. FIG. 4 shows the pant diaper 55 as it appears when the side seams 65 have been formed and the tensioned elastic elements have been allowed to relax and gather the chassis material to form elasticized leg and waist openings 67,66.

The front and back panels 56,57 are constituted by a reinforced elastic laminate 68 in accordance with the invention and comprising at least one creped nonwoven layer. The front and back panels 56,57 are elastically stretchable at least in the direction of the waist edges 62.

The crotch panel 58 is formed from a nonwoven crotch material 69 that has been joined to the front and back panels 56,57 at crotch seams 70. Hence, the crotch material 69 which preferably is a non-elastic material, such as a non-elastic nonwoven material, is arranged in the core region 59 of the article and overlaps slightly with the elastic front and back panels 56,57. The crotch material 69 is joined along its transverse edges 71,72 to the front and back panels 56,57 at the overlapping portions. The joining can be made in any suitable way such as by ultrasonic welding, adhesively or similar. In alternative embodiments of the invention, an outer nonwoven material may extend continuously over the front and back panels 56, 57 and the crotch panel 58 so that no seams or joins are needed between the panels 58,56,57.

In the shown example, the elastic waist band 61 comprises first and second plies of substantially non-elastic nonwoven material that is elasticized by one or more elongate elastic members 73, such as elastic threads or bands. The first and second plies can be formed from a single layer of material that is folded over onto itself or can be made from two separate strips of material. The elastic members 73 are arranged in the waist band 61 in a tensioned state such that they contract and gather the nonwoven material in the waist band 61 when they are allowed to relax, as shown in FIG. 9.

The elastic waist band 61 is secured to the front and back panels 56,57 with the elastic members 73 in an extended state and with the material in the front and back panels sandwiched between the nonwoven plies in the waist band. Alternatively, the elastic waist band 61 can be a component that is prefabricated and joined to the outside or the inside of the front and back panels 56,57 respectively. The waist band join 74 between the waist band 61 and the front and back panels 56,57 can be made in any suitable way such as by means of ultrasonic welding, heat welding, or adhesively. A further option is to create the waist band 61 from one or more non-elastic nonwoven layers that are also parts of the front and back panels 56,57 and form continuous extensions thereof. It is also conceivable to form an elastic waist feature by double-folding portions along the waist edges 62 of the elastic front and back panels 56,57 and optionally supplementing the folded portions by additional elastic elements. Suitable elastic waist bands are also disclosed in PCT/SE205/000309.

Elastic members 75 are also arranged at the edges of the leg openings 67 and serve to elasticize the leg openings. The elastic members at the leg openings can be any kind of conventional elastic elements such as elastic threads, bands, foam strips, or similar. One example of a suitable way of arranging leg elastics is disclosed in WO 2004/078083.

The planar extension of the core region 59 is defined by a liquid-impervious barrier sheet 76 arranged between an absorbent core 77 and the chassis 60.

The liquid-impervious barrier sheet 76 has rectangular shape and the absorbent core 77 is hour-glass shaped. A liquid permeable topsheet 78 is arranged over the core 77 and the liquid-impervious barrier sheet 76. Hence, the liquid-impervious barrier sheet 76 underlies the absorbent core 77 and the adjacent areas immediately outside the absorbent core 77.

The liquid-permeable topsheet 78 can consist of any material known for the purpose, such as a layer of nonwoven material, a perforated plastic film, net material, tow, or the like. The topsheet 78 can, of course, also consist of a laminate of two or more sheets of the same or different materials.

The liquid-impervious barrier sheet 76 can consist of a liquid-impermeable plastic film, a nonwoven sheet which has been coated with a liquid barrier material, or some other flexible material sheet which has the ability to withstand liquid penetration. However, it can be advantageous if the liquid-impervious barrier sheet 76 is breathable, i.e. permits the passage of water vapour through the sheet 76.

The absorption core 77 can be made of absorbent material, such as cellulose fluff pulp, tissue, absorbent foam, etc. It is also possible for the absorption core to contain superabsorbents, i.e. polymer materials which are able to absorb body fluid corresponding to many times their own weight and form a hydrogel. Such superabsorbents are usually present in the form of particles, but fibres, flakes, granules and films are also available. Moreover, the absorption core 77 can comprise nonabsorbent components such as stiffening elements, shaping elements, binders, etc. Various types of liquid-receiving porous structures such as fibre wadding, resilient nonwoven webs, open-cell foam or the like can also be included in the core. It is, of course, also possible to use absorption cores 77 having other shapes than that shown in FIGS. 3 and 4.

The topsheet 78, barrier sheet 76 and absorption core 77 may have been formed as a separate component or "core pack" that has subsequently been integrated in the diaper chassis. The various components included in the core pack can be connected to one another in any conventional manner, for example by adhesive bonding, ultrasonic welding or thermowelding. The core pack can of course contain further components in addition to those described here, such as a liquid transport sheet, elastic members, shape-stabilizing members, shaping elements or the like.

The nonwoven material 69 in the crotch panel 58 is arranged on the garment-facing side of the liquid-impervious barrier sheet 76. The core region 59 extends into the front and back panels 56,57 so that the elastic laminate 68 in these panels overlap with the liquid-impervious barrier sheet 76 in the outer parts of the core region 59 as seen in FIG. 3. The elastic laminate 68 is arranged on the garment-facing side of the liquid-impervious barrier sheet 76.

As shown in FIGS. 3 and 4, the elastic reinforced laminate 68 preferably forms the front and the back panels 56,57 of the pant diaper 55. However, it is possible to make only parts of the respective front and back panel 56,57 of the elastic laminate 68 with the creped nonwoven. In such embodiments, at least 20%, preferably at least 25%, more preferably at least 30% and most preferably at least 40% of the total surface area of the chassis as seen in the flat state shown in FIG. 3 is constituted by the elastic laminate in accordance with the invention. As an example, the elastic laminate may be used only in those parts of the front and back panels 56,57 that are intended to lie over the wearer's hips and thus form elastic side panels. In some instances, it may be desirable to avoid any overlap between the core region 59 and the elastic laminate material in the front and back panels 56,57.

Hence, the invention relates to a pant-type absorbent article (55) comprising a chassis structure, the chassis structure comprising a front panel (56), a back panel and a crotch panel (58) arranged between the front and back panels (56,57) and front and back waist panels (61a,61b) arranged at the front and back panels (56,57) respectively, wherein at least one of the front and back panels (56,57) comprises an activated three-layer elastic laminate (68) comprising a first fibrous nonwoven web and a second fibrous nonwoven web and an elastic film between the first and second fibrous nonwoven webs. As set out above, at least one of the first and second fibrous nonwoven webs is a creped nonwoven web.

Description of Test Methods
Tensile Strength (Reference: ASTM D 882)

The method measures tensile strength and elongation of different elastic materials. The tensile strength and elongation of a well-defined test piece is tested by means of a tensile tester.

Apparatus: Instron 456
   Tensile tester connected to a computer
   Crosshead speed: 500 mm/min
   Clamp distance: 50 mm Sample preparation: Test samples are cut from the entire width of the material. The width of the sample shall be 25.4 mm and the length at least 50 mm longer than the clamp distance if possible. It is of importance that the edges of the sample are even and without break notches. The samples are conditioned for at least 4 h in 50% RH±5% RH and 23° C.±2° C. before testing.

Procedure: The tensile tester is calibrated according to the apparatus instructions and set to zero. The sample is mounted and it is ensured that it is not obliquely or unevenly fastened. The material is prevented from slipping by using clamps covered with galloon or similar material. The tensile tester is started, and stopped after the material has broken (if not automatically controlled). Measurements resulting from premature failure (i.e. the sample breaks at the clamp, or is damaged during preparation) are ignored, if possible.

The following results are expressed by the tensile tester/computer:
   Maximum force, N/25.4 mm
   Elongation at maximum force, %
   Break force, N/25.4 mm
   Elongation at break force, %
   Knee point, N %

Elasticity Test

The method measures how an elastic material behaves at cycles of repeated load and unload. The sample is stretched to a predetermined elongation and a cyclic movement between 0 and said predetermined elongation is performed. Desired load and unload forces are recorded. The permanent, i.e. remaining, elongation of the relaxed material is measured.

A tensile tester, Lloyd LRX, able to perform cyclic movements and equipped with a printer/plotter or software presentation is used. The sample is prepared by cutting it to a width of 25 mm and a length that is preferably 20 mm longer than the distance between the clamps in the tensile tester.

The tensile tester is calibrated according to the apparatus instructions. The parameters needed for the test (load and unload forces) are adjusted to:

| | |
|---|---|
| Crosshead speed: | 500 mm/min |
| Clamp distance: | 50 mm |
| Preload: | 0.05 N |

The sample is placed in the clamps according to the marks and it is made sure that the sample I centred and fastened perpendicularly in the clamps.

The tensile tester is started and three cycles between 0 and the predetermined elongation equal to the highest defined 1$^{st}$ load are performed. Before the last cycle, the sample is relaxed for 1 minute, and then the permanent elongation is measured by stretching the sample until a force of 0.1 N is detected and the elongation is read.

An elastic material is defined as a material having a permanent elongation after relaxation of less than 10% after the material has been subjected to an elongation of 30% in the test above. An elongation of 30% means an elongation to a length that is 30% longer than the initial length of the sample.

A non-elastic material has a permanent elongation after relaxation of more than 10% after having been subjected to an elongation of 30%.

Puncture Strength

Puncture strength is measured according to ASTM Designation D3763-02. From penetration impact-type tests, this method produces data of load versus displacement. The maximum load for each sample is calculated.

EXAMPLES

The tensile strength in the cross direction (CD) and the puncture strength was measured for two samples.

Sample A was an activated three-layer laminate comprising an inner apertured three-layer elastomeric film of PE-SEBS-PE, basis weight 36 g/m$^2$ and two outer layers of non-creped nonwoven material, BB Sofspan 200 with a basis weight of 22 g/m$^2$ on each side of the film.

Sample B was a three-layer laminate comprising an inner apertured three-layer elastomeric film of PE-SEBS-PE, basis weight 36 g/m$^2$ and a first outer layer of nonwoven material, BB Sofspan 200 with a basis weight of 22 g/m$^2$ on one side of the film and a second outer layer of a creped nonwoven spunbond having a basis weight of 20 g/m$^2$ on the other side of the film. The creped nonwoven was compacted to 50% at creping.

The test results are shown in Table 1, below.

TABLE 1

| Sample | Tensile strength CD N/25 mm | Puncture force N |
|---|---|---|
| A | 10 | 40 |
| B | 18 | 48 |

As can be seen in Table 1, laminates B in accordance with the invention has considerably higher CD tensile strength and higher puncture resistance than the prior art three-layer laminate.

The invention claimed is:

1. A pant absorbent article comprising a chassis structure, the chassis structure comprising a front panel having a front end edge and first and second side edges, a back panel having a back end edge and first and second side edges, a crotch panel arranged between the front and back panels, and front and back waist panels arranged at the front and back panels respectively, and an absorbent core being integrated with the chassis structure, the first and second side edges of the front panel being joined by edge joins to the corresponding first and second side edges of the back panel, wherein at least one of the front and back panels comprises an activated three-layer elastic laminate comprising a first fibrous nonwoven web and a second fibrous nonwoven web and an elastic film between the first and second fibrous nonwoven webs, wherein at least one of the first and second fibrous nonwoven webs is a creped nonwoven web and in that the three-layer elastic laminate has a tensile strength in a first direction of at least 20 N/25 mm and a tensile strength in a second direction perpendicular to the first direction of at least 15 N/25 mm.

2. The pant absorbent article according to claim 1, wherein at least one of the waist panels is an elastic waist panel.

3. The pant absorbent article according to claim 2, wherein the elastic waist panel extends continuously all the way between the edge joins.

4. The pant absorbent article according to claim 1, wherein at least 20%, of the total surface area of the chassis as seen in a flat state is constituted by the activated elastic three-layer laminate.

5. The A pant absorbent article according to claim 4, wherein at least 40% of the total surface area of the chassis as seen in a flat state is constituted by the activated elastic three-layer laminate.

6. The pant absorbent article according to claim 1, wherein the absorbent core is a part of a core component, the core component comprising a topsheet, a barrier sheet and the absorption core arranged between the topsheet and the barrier sheet.

7. The pant absorbent article according to claim 1, wherein the elastic film in the activated three-layer elastic laminate is bonded to at least one of the first and second fibrous nonwoven webs by extrusion coating.

8. The pant absorbent article according to claim 1, wherein at least one of the first and second nonwoven webs is adhesively, thermally or ultrasonically bonded to the elastic film.

9. The pant absorbent article according to claim 1, wherein the elastic film in the activated three-layer elastic laminate is perforated.

10. The pant absorbent article according to claim 1, wherein the activated three-layer elastic laminate has been continuously produced from webs running in a machine direction and the activated three-layer elastic laminate has been activated by incremental stretching at least in the machine direction.

11. The pant absorbent article according to claim 1, wherein the first and/or second fibrous nonwoven web in the activated three-layer elastic laminate comprises thermoplastic fibres.

12. The pant absorbent article according to claim 11, wherein the first and/or second fibrous nonwoven web comprises at least 50% thermoplastic fibres.

13. The pant absorbent articles according to claim 12, wherein the first and/or second fibrous nonwoven web comprises at least 80% thermoplastic fibres.

14. The pant absorbent article according to claim 1, wherein the three-layer elastic laminate has a tensile strength in the first direction of at least 25N/25 mm or a tensile strength in the second direction of at least 20N/25 mm.

15. The pant absorbent articles according to claim 1, wherein the activated three-layer elastic laminate is prepared by:
  (i) bonding the first fibrous nonwoven web, the second fibrous nonwoven web and the elastic film, wherein all the layers are unstretched during the bonding process, and
  (ii) stretching the bonded laminate through intermeshing gears, thereby rendering elastic the three layer laminate.

\* \* \* \* \*